(12) United States Patent
Matsumoto

(10) Patent No.: US 7,732,635 B2
(45) Date of Patent: Jun. 8, 2010

(54) METHOD FOR PRODUCING ORGANIC ACID

(75) Inventor: Hajime Matsumoto, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 558 days.

(21) Appl. No.: 11/783,164

(22) Filed: Apr. 6, 2007

(65) Prior Publication Data

US 2007/0238898 A1  Oct. 11, 2007

(30) Foreign Application Priority Data

Apr. 7, 2006  (JP) .............................. 2006-106808

(51) Int. Cl.
 *C07C 51/16* (2006.01)
(52) U.S. Cl. ...................... 562/523; 562/545
(58) Field of Classification Search ................. 562/523, 562/545
See application file for complete search history.

(56) References Cited

U.S. PATENT DOCUMENTS

| | | | |
|---|---|---|---|
| 4,530,826 | A | 7/1985 | Ohashi et al. |
| 5,315,037 | A | 5/1994 | Sakamoto et al. |
| 5,817,865 | A | 10/1998 | Machhammer et al. |
| 6,831,195 | B2 | 12/2004 | Nishimura et al. |
| 7,038,081 | B2 | 5/2006 | Matsumoto et al. |
| 2003/0045749 | A1 | 3/2003 | Nishimura et al. |
| 2003/0181621 | A1 | 9/2003 | Matsumoto et al. |

FOREIGN PATENT DOCUMENTS

| | | |
|---|---|---|
| EP | 1 346 974 | 9/2003 |
| JP | 57-93946 | 6/1982 |
| JP | 58-214605 | 12/1983 |
| JP | 5-17377 | 1/1993 |
| JP | 5-246941 | 9/1993 |
| JP | 7-65818 | 3/1995 |
| JP | 9-227445 | 9/1997 |
| JP | 11-83232 | 3/1999 |
| JP | 2002-266656 | 9/2002 |
| JP | 2003-73327 | 3/2003 |
| JP | 2003-268011 | 9/2003 |

OTHER PUBLICATIONS

Office Action issued Apr. 30, 2008 (with English translation) in Japanese Patent Application No. 2006-106808 corresponding to the present U.S. application.
Kagaku Daijiten 2 (Chemical comprehensive dictionary 2) p. 813, 1989.
Kagaku Daijiten 7 (Chemical comprehensive dictionary 7) p. 2, 1989.
Office Action issued Sep. 16, 2008 (with English translation) in Japanese Patent Application No. 2006-106808 corresponding to the present U.S. application.
Abstract of JP 5-17377 published Jan. 26, 1993.

*Primary Examiner*—Taylor Victor Oh
(74) *Attorney, Agent, or Firm*—Wenderoth, Lind & Ponack, L.L.P.

(57) ABSTRACT

The utilization amount of steam generated by heat recovery tends to decrease in a production process of an organic acid when the concentration of an organic acid solution obtained in a step of collecting an organic acid with a solvent such as water becomes high. The purpose of the invention is to find an advantageous method for effectively utilizing reaction heat and contribute to global environmental preservation and saving product costs. The present invention provides a production method of an organic acid comprising carrying out a gas-phase catalytic oxidation reaction of raw material gas at the temperature from 250° C. to 450° C., recovering at least a part of reaction heat and/or heat generated in combustion of a waste as high pressure steam at a pressure of 1 MPaG or higher, supplying at least a part of the high pressure steam to a back pressure steam turbine connected with a blower to drive the blower, and supplying at least a part of discharged gas from the back pressure steam turbine, low pressure steam A at a pressure lower than 1 MPaG, to an absorption type refrigerator to utilize the low pressure steam A as a heat source of the absorption type refrigerator.

20 Claims, No Drawings

METHOD FOR PRODUCING ORGANIC ACID

FIELD OF THE INVENTION

The present invention relates to a production method of an organic acid such as acrylic acid while utilizing reaction heat generated in a gas-phase catalytic oxidation reaction effectively. Particularly, the invention relates to a production method of the organic acid with high heat efficiency and high production efficiency by effective utilization of steam which is produced by a large quantity of heat generated in the gas-phase catalytic oxidation reaction and heat generated in combustion of a by-product of waste gas and waste oil from the production of the organic acid.

BACKGROUND ART

The inventor of the present invention has been producing organic acids (for example, acrylic acid) by a gas-phase catalytic oxidation reaction. Since a large quantity of waste heat is generated in a large scale chemical plant as well as in a chemical plant for carrying out a gas-phase catalytic oxidation reaction, efforts have been made to use the waste heat as efficiently as possible by introducing heat utilization techniques.

For example, Japanese Patent Application Laid-Open (JP-A) H7-65818 discloses a technique concerning to a method for recovering waste heat from cooling water in a fuel cell equipment. According to this technique, steam is obtained from cooling water used for heat removal at the time of a fuel cell generating power, and then the steam is supplied to a waste gas turbine power generator, and at the same time the steam is supplied to an absorption type refrigerator to obtain cold water. JP-A-2002-266656 discloses a technique concerning to a gas turbine cogeneration system. According to this technique, warm water produced by using waste gas passed through a waste heat recovery boiler is utilized to a driving heat source for an adsorption type refrigerator. In the technique of JP-A-2002-266656, cold water is used for cooling air sucked into the turbine.

Waste heat is also utilized in an organic compound production plant. JP-A-S57-93946 discloses a technique of driving an absorption type refrigerator or the like by using a heat source of 90° C. or less, which obtained in an ammoxidation process at the temperature of about from 100° C. to 130° C., as a driving source. JP-A-H5-17377 discloses a technique of utilizing heat on production of styrene.

Further, waste heat utilization in a waste incinerator, although not in a chemical plant, has been discussed. JP-A-H11-83232 discloses a technique of producing steam by a boiler using combustion gas generated in a waste incinerator, driving a turbine of a power generator by the steam to generate electric power, at the same time using a part of low temperature steam exhausted from the turbine as a driving heat source for a lithium bromide absorption type refrigerator, and using a part of high temperature steam at the inlet of the turbine as a driving heat source for an ammonia absorption type refrigerator.

However, the techniques described in the above-mentioned JP-A-H7-65818, JP-A-2002-266656, JP-A-S57-93946, JP-A-H5-17377, and JP-A-H11-83232 are not methods for utilizing waste heat in an organic acid production by a gas-phase catalytic oxidation reaction. Thus, it cannot say that it is appropriate to apply these techniques to an organic acid production plant as they are.

In the case of carrying out a gas-phase catalytic oxidation reaction, it is required to supply a raw material in gas phase. For example, propylene liquid as a raw material is gasified through an evaporator and supplied to a reactor in the case of acrylic acid production. When a raw material such as propylene or the like is subjected to a gas-phase catalytic oxidation with molecular oxygen-containing gas in the presence of a gas-phase catalytic oxidation reaction catalyst, produced gas containing an aimed organic acid and by-products as well is obtained and at the same time a large quantity of reaction heat is generated. Generally, the reaction heat is recovered by heat exchange.

In the successive step, the gas produced by the gas-phase catalytic oxidation is led to an absorbing column of an organic acid and contacted with a solvent (generally water is used) for collecting the organic acid to be cooled, absorbed, and collected. The obtained solution containing the organic acid and by-products is successively refined by a method such as distillation and crystallization to obtain the refined organic acid.

With respect to utilization of reaction heat generated in an organic acid production by such gas-phase catalytic oxidation reaction, the inventor has already been examining. For example, the inventor applied an invention for a patent of JP-A-2003-73327 which discloses a method of recovering heat (including reaction heat) generated in an acrylic acid production plant as steam and using the heat as heat energy, mechanical energy, or electric energy. The inventor also applied an invention for a patent of JP-A-2003-268011 which discloses a method of using steam or cold liquid, which is generated in a production process of acrylic acid, in a poly (acrylic acid) production plant.

Recently, collecting efficiency in an absorbing column of an organic acid has been improved to obtain high concentration acrylic acid aqueous solution. Conventionally, as a post-process of collecting acrylic acid, refining has been carried out by steps which are combined of dehydration distillation, distillation for removing high boiling point impurities, acrylic acid recovery distillation, aldehyde-removal distillation and the like, and low pressure steam recovered in a reaction step and the like has been utilized for the distillation steps. However, when the high concentration acrylic acid aqueous solution comes to be obtained, the number of the succeeding distillation steps and time taken for the steps can be saved, and used amount of the steam recovered in an acrylic acid production plant tends to be decreased accordingly.

In an organic acid ester production step or in a crystallization step which is involved in the refining steps, a large quantity of cold water (brine) is required. To produce the cold water, a refrigerator has been driven by using commercial electric power or by generating electric power by rotating a turbine of a power generator by steam. However, in the first case, cost becomes high, and in the other case, electric power generation efficiency cannot be high. The above-mentioned JP-A-2003-268011 implies use of an absorption type refrigerator, however, it is not mentioned how to use the refrigerator.

Accordingly, the purpose of the invention is to find a more specific and practical method of an effective utilization of reaction heat than methods disclosed in JP-A-2003-73327 and JP-A-2003-268011, and to provide a production method of an organic acid that is favorable to global environmental preservation and saving production cost.

DISCLOSURE OF THE INVENTION

First invention of the application is a production method of an organic acid comprising carrying out a gas-phase catalytic oxidation reaction of raw material gas at the temperature from 250° C. to 450° C., recovering at least a part of reaction heat and/or heat generated in combustion of a waste as high pressure steam at a pressure of 1 MPaG (G means gauge pressure, hereinafter the same) or higher, supplying at least a part of the high pressure steam to a back pressure steam turbine connected with a blower to drive the blower, and supplying at least a part of discharged gas from the back pressure steam turbine, low pressure steam A at a pressure lower than 1 MPaG, to an absorption type refrigerator to utilize the low pressure steam A as a heat source of the absorption type refrigerator.

Second invention of the application is a production method of an organic acid comprising carrying out a gas-phase catalytic oxidation reaction of raw material gas at the temperature from 250° C. to 450° C., recovering at least a part of reaction heat and/or heat generated in combustion of a waste as low pressure steam B at a pressure lower than 1 MPaG, and supplying at least a part of the low pressure steam B to an absorption type refrigerator to utilize the low pressure steam B as a heat source of the absorption type refrigerator.

Third invention of the application is a production method of an organic acid comprising carrying out a gas-phase catalytic oxidation reaction of raw material gas at the temperature from 250° C. to 450° C., recovering at least a part of reaction heat and/or heat generated in combustion of a waste as high pressure steam at a pressure of 1 MPaG or higher, supplying at least a part of the high pressure steam a back pressure steam turbine connected with a blower to drive the blower, recovering at least a part of the reaction heat and/or the heat generated in combustion of a waste as low pressure steam B at a pressure lower than 1 MPaG, and supplying at least a part of the low pressure steam B and at least a part of discharged gas from the back pressure steam turbine, low pressure steam A at a pressure lower than 1 MPaG, to an absorption type refrigerator to utilize the low pressure steam A and B as a heat source of the absorption type refrigerator.

It is also preferable to supply at least a part of the low pressure steam A and/or the low pressure steam B to a condensing steam turbine of a power generator to obtain electric power.

In addition, heat from a reactor for the gas-phase catalytic oxidation reaction may be recovered by a heat medium, and the high pressure steam at a pressure of 1 MPaG or higher may be produced by using the heat medium after recovering the heat from the reactor.

Further, the production method of the invention is preferable to include a step of collecting gas of an organic acid, a product of the gas-phase catalytic oxidation reaction, with a liquid medium to produce an organic acid solution containing 80 mass % or more of the organic acid, successively to a step of the gas-phase catalytic oxidation reaction. It is also a preferable aspect of the invention that the method further includes a cooling step using a coolant obtained in the absorption type refrigerator; the method wherein the cooling step comprises a crystallization step of an organic acid; or the method wherein the organic acid is (meth)acrylic acid.

According to the invention, various kinds of heat generated in the production process of an organic acid by the gas-phase catalytic oxidation reaction are recovered as steam, and mechanical energy is obtained directly from the steam or the steam is directly used as a heat source for an absorption type refrigerator. Therefore, the steam can be utilized more effectively than in the case of utilizing the steam to obtain electric power for a power source of mechanical energy or an absorption type refrigerator.

DETAILED DESCRIPTION OF THE INVENTION

The production method of an organic acid of the present invention includes a step of a gas-phase catalytic oxidation reaction of raw material gas carried out at the temperature from 250° C. to 450° C. If the temperature is within a range from 250° C. to 450° C., heat can be utilized efficiently. The raw material gas to be subjected to the gas-phase catalytic oxidation may be propane, propylene(meth)acrolein, isobutylene, xylene, naphthalene, benzene, butane, or the like. They may be subjected to the gas-phase catalytic oxidation with molecular oxygen-containing gas to produce (meth)acrylic acid, phthalic acid, maleic acid or the like.

Hereinafter, the production method of an organic acid of the present invention will be described along with a production method of acrylic acid using propane and/or propylene (hereinafter, represented by "propylene") as a raw material. However, it is not intended that the invention will be limited to the following production method, and the invention may be applied to the gas-phase catalytic oxidation reaction of the above-mentioned raw material gases. Further, the following production method may be modified appropriately unless the effect of the invention is impaired. Accordingly, it is not intended that steam generated in the production process of the organic acid be limited to the following kinds, and the invention may be applied preferably to use of steam other than the exemplified kinds.

In the production method of acrylic acid using propane and/or propylene as a raw material, the gas-phase catalytic oxidation reaction of propylene with molecular oxygen is carried out. The concentration of the raw material gas, the concentration of propylene, is preferably 7% to 15% by volume, and the water concentration is preferably adjusted to be in a range from 0% to 10% by volume. The molecular oxygen is preferably adjusted to satisfy a propylene/molecular oxygen ratio by volume in a range from 1/1.0 to 1/2.0. The molecular oxygen to be used may include, for example, air, oxygen-enriched air, and pure oxygen. A gas-phase catalytic oxidation reactor is not particularly limited, however, a multitubular reactor which is excellent in heat exchange efficiency is recommended.

The operation conditions of the reactor are not particularly limited. For example, in the case of carrying out a two-stage gas-phase catalytic oxidation reaction in the reactor, acrolein-containing gas is produced from supplied gasified propylene in a first stage catalyst layer of the reactor. Temperature of the reaction is controlled in a range from 250° C. to 450° C., and for example, it is recommended to control a pressure of the reaction in a range from 0 MPaG to 0.5 MPaG, and a space velocity in a range from 300 $h^{-1}$ to 5000 $h^{-1}$ (STP) in respect of improving reaction efficiency. The acrolein-containing gas produced in the first stage catalyst layer is then introduced into a second stage catalyst layer of the reactor to produce acrylic acid-containing gas. Temperature of the reaction in the second stage catalyst layer is controlled in a range of preferably 250° C. or more and 380° C. or less, and more preferably 300° C. or less. A pressure of the reaction is preferably controlled in a range from 0 MPaG to 0.5 MPaG, and a space velocity is preferably controlled in a range from 300 $h^{-1}$ to 5000 $h^{-1}$ (STP). A catalyst packed in the reactor may be an oxidation catalyst commonly used in the production of acrylic acid for both of the first stage and the second stage. The production method of the acrylic acid-containing gas is not limited to the two-stage gas-phase catalytic oxidation reaction and may be adopted conventionally known acrylic acid-containing gas production methods of one-stage or a plurality of stages.

As described above, when gasified propylene is subjected to gas-phase catalytic oxidation, reaction heat is generated since the reaction is an exothermal reaction. Therefore, a heat medium of predetermined reaction temperature (for example, 250° C. or more and 450° C. or less) is supplied to a shell side of the first stage reactor and the second stage reactor to remove the reaction heat from the tubes. A part of the heat medium heated by absorption of the reaction heat is discharged out and supplied to a steam generation apparatus (a heat medium boiler) to generate steam. The heat medium which is cooled by transferring heat to water may be circulated again to the shell sides of the reactor. In a similar way, in the second stage reactor, the heat medium is circulated and supplied to the steam generation apparatus. An inorganic type molten salt such as a mixture of potassium nitrate and sodium nitrite; and a mixture of potassium nitrate, sodium nitrite and sodium nitrate (HTS: so-called "niter"; for example, NeoSK-SOLT manufactured by Soken Tecnix Co., Ltd.); and an organic type heat medium such as Dowtherm (manufactured by Dow Chemical Company) may be used as the heat medium.

It is preferable that the steam generation apparatus is installed in common to the first stage reactor and the second stage reactor to generate high pressure steam in respect of effective utilization of the heat, however, low pressure steam may be generated from the beginning. Further, the steam generation apparatus may be installed independently in each of the first stage reactor and the second stage reactor. For example, high pressure steam may be generated in the first stage rector and low pressure steam may be generated in the second stage reactor. Herein, high pressure steam means steam at a pressure of 1 MPaG or higher and low pressure steam means steam at a pressure lower than 1 MPaG.

The steam generation apparatus used in the invention is not particularly limited and conventionally known heat medium boilers such as, for example, a cylindrical boiler, a natural circulation water tube boiler, a forced circulation boiler, a once-through boiler and the like may be used.

The steam pressure in the steam generation apparatus may be selected without any limitation in a range higher than a steam pressure equivalent to a solidification point of the heat medium and lower than a steam pressure equivalent to the temperature of the heat medium. However, the steam pressure is preferably 1 MPaG or higher and more preferably 1.5 MPaG or higher, because high pressure steam is more efficient in use of the generated steam. Although the upper limit of the steam pressure is not particularly limited, the steam pressure is preferably 4.8 MPaG or lower and more preferably 4.5 MPaG or lower. When the steam pressure is too low, the temperature of the steam closes to the solidification point of the heat medium. Accordingly, in this case, the heat medium is easily to be solidified and the viscosity of the heat medium is also increased, and then heat transfer efficiency may be decreased. As a result, the apparatus has to be enlarged in order to recover heat efficiently. On the other hand, when the steam pressure is too high, the designed pressure is increased to result in higher cost of the apparatus. Further, in the case of high pressure, the temperature difference between the steam and the heat medium is small, and therefore, the heat transfer area of the apparatus becomes large.

The means of pressure control in the steam generation apparatus should not be particularly limited and, for example, a valve (a control valve) may be exemplified. The pressure in the steam generation apparatus can be measured by properly installing a pressure gauge, a pressure sensor or the like such as, for example, a Bourdon-tube type, a diaphragm type or the like at a proper point. The temperature in the steam generation apparatus can be measured by properly installing a thermoelectric thermometer, a resistance thermometer, an expansion thermometer or the like in a proper point of pipes or appliances. In addition, a control part may be combined to be capable of controlling the pressure automatically by using a detection part such as the above-mentioned pressure gauge, thermometer and the like and an operation part such as the pressure control valve and the like.

In the case that the reaction heat is recovered as high pressure steam (the temperature is not particularly limited, however, generally a range from 183° C. to 270° C.) at a pressure of 1 MPaG or higher (more preferably 1.5 MPaG or higher), all or a part of the high pressure steam is superheated to the temperature of over 183° C. to 450° C. by heat exchange with the heat medium of high temperature, if necessary, and supplied to a back pressure steam turbine connected with a blower for supplying molecular oxygen to the reactor. The high pressure steam rotates the turbine, so that a blower fan also rotates to be capable of supplying the molecular oxygen to the reactor. In addition, in the case that excess motive power remains after the high pressure steam is supplied to the back pressure steam turbine to obtain blower driving motive power, the excess motive power may be used for generating electric power. The obtained electric power may be used in the production process.

The steam which supplies a rotating energy to the back pressure steam turbine becomes low pressure superheated steam at the temperature about from 120° C. to 300° C. and a pressure of about from 0.1 MPaG to 1.0 MPaG (hereinafter, called as low pressure steam A) is discharged. In the invention, at least a part of the low pressure steam A is utilized as a heat source for a regenerator of an absorption type refrigerator. Further, a part of the remaining is preferably utilized as a heat source for a re-boiler in a distillation step for refining acrylic acid. In this case, it is preferable that water is supplied to the low pressure steam A to make a saturated steam at the temperature from 120° C. to 183° C. It is because undesired polymerization of acrylic acid or the like is caused if the temperature is too high, and also heat transfer efficiency of the saturated steam is better in the case that a multi-tubular heat exchanger is used as the regenerator or the re-boiler. As the method of supplying water to the low pressure steam A, water may be conveyed by a pump or the like to the middle of a line in which the discharged gas from the back pressure steam turbine is supplied to the regenerator of the absorption type refrigerator (or to the re-boiler in a distillation step).

As the absorption type refrigerator, conventionally known facilities capable of carrying out cycles of evaporation→absorption→regeneration→condensation→evaporation of a coolant may be employed. Water, ammonia, and the like may be used as the coolant, and lithium bromide, water, and the like may be used as an absorption liquid for the absorption. The regenerator evaporates the coolant from the absorption liquid diluted with the coolant and recovers the absorption liquid, and the low pressure steam A is utilized for a heat source for evaporation.

Cold water obtained in the absorption type refrigerator can be used for a cooling step in the production process of acrylic acid and in other polymerization processes of acrylic acid ester or acrylic acid. In the cooling step, a condenser, a cooler or the like may be employed. In the case of carrying out crystallization in a refining step of acrylic acid, the cold water may be used for the crystallization step. As the cold water, an aqueous solution of ethylene glycol, an aqueous solution of methanol and the like besides water alone may be used.

In the case that excess low pressure steam A remains after the low pressure steam A is used as a heat source for the regenerator of the absorption type refrigerator and the re-boiler in the distillation step, the low pressure steam A may be supplied to a condensing steam turbine to recover energy of the steam as electric power. The recovered electric power may be used as an electric power source for a pump and the like in the production process of acrylic acid. Accordingly, no steam is purged without avail and almost all of the steam recovered from the reaction heat generated in the gas-phase catalytic oxidation reaction can be effectively utilized.

On the other hand, in the case that low pressure steam (hereinafter, called as low pressure steam B) is generated instead of the high pressure steam in the steam generation apparatus, at least a part of the low pressure steam B is preferably utilized as a heat source for the regenerator of the absorption type refrigerator or the re-boiler in the distillation step, similarly to the case of utilizing the low pressure steam A. If there remains excess low pressure steam B, similarly to the above-mentioned case, the low pressure steam B is supplied to a condensing steam turbine to recover electric power.

In the case that the steam generating apparatus is installed independently in each of the first stage reactor and in the second stage reactor, the high pressure steam may be generated in the first stage reactor and the low pressure steam B may be generated in the second stage reactor, for instance (needless to say, the installation vice versa is allowed, however the reaction condition in the first stage reactor is generally suitable for obtaining the high pressure steam). In this case, the high pressure steam obtained in the first stage reactor is supplied to the back pressure steam turbine connected with a blower to use for driving the blower as described above. A part of the discharged gas (low pressure steam A) and the low pressure steam B obtained in the second stage reactor may be used for a heat source for the regenerator of the absorption type refrigerator and a part of the remaining may be used for the re-boiler in the distillation step. If excess low pressure steam A and/or B still remains, it may be converted into electric power by the condensing steam turbine.

In the invention, heat of the product gas produced in the reactor may be recovered. In this case, it is preferable that the product gas may be supplied to a waste heat boiler to recover the heat of the reaction product gas before supplied to an absorbing column and low pressure steam is generated. The operation temperature of the waste heat boiler is preferably 140° C. or more, because if it is lower than 140° C., clogging in equipments may occur by deposition of easy-to-clog substances. The low pressure steam generated in the waste heat boiler may be used for a heat source for the regenerator of the absorption type refrigerator or the re-boiler in the distillation step, or may be supplied to the condensing steam turbine, similarly to the aforementioned low pressure steam A or the low pressure steam B. It is also possible to recover high pressure steam in the waste heat boiler, and so steam is properly selected based on operation conditions.

The reaction product gas passed through the waste heat boiler is supplied to an absorbing column. The type of the absorbing column is not particularly limited. For example, trays such as a bubble cap tray, a sieve tray, a valve tray, a dual flow tray, a baffle tray, a ripple tray or the like packing regular fillers of a gauze type, a sheet type, a grid type or the like, or irregular fillers may be usable.

As a collecting solvent, water, low boiling point solvents such as organic acid-containing water, and high boiling point solvents such as diphenyl ether and diphenyl may be used.

The mass flow rate of the collecting solvent is preferably 0.1 times to 1.5 times to that of acrylic acid contained in the reaction product gas. When the ratio of the mass flow rate (solvent/acrylic acid) is lower than 0.1 times, the loss of acrylic acid may be possibly increased. On the other hand, when the ratio of the mass flow rate (solvent/acrylic acid) exceeds 1.5 times, it becomes difficult to obtain a high concentration acrylic acid solution and therefore it is not preferable.

If water is used as the collecting solvent, acrylic acid in the reaction product gas is caught in water to give an aqueous solution of acrylic acid with the acrylic acid concentration of about from 50 mass % to 98 mass %. The aqueous solution is supplied to a succeeding refining step, and dehydrated and refined in a step of distillation, crystallization or the like. In terms of downsizing of equipments necessary for the refining step and saving of energy consumption, it is preferable that the concentration of acrylic acid in the aqueous solution is 80 mass % to 98 mass %. In the case that the concentration of acrylic acid is 80 mass % to 98 mass %, the consumption of the steam obtained from the reaction heat or the like become relatively small in the refining step. In the present invention, however, as described above, the excess steam is advantageously used as a heat source for the absorption type refrigerator or for power generation by driving the turbine, and is not discharged without avail. When the concentration of acrylic acid is 80 mass % to 98 mass %, a part of the gas discharged from the top of the absorbing column is preferably recycled to the reactor in order to lower the loss of acrylic acid. It is recommended that the gas to be recycled is cooled by a condenser before the gas is turned back to the reactor. This is because the amount of water to be led to the reactor can be decreased.

In the present invention, heat generated in combustion of a waste can be used as the heat source for steam generation. The waste means a part of waste gas discharged from the top of the absorbing column (a part of the gas is preferably recycled to the absorbing column after being cooled in a condenser) and waste gas and/or waste solution separated in the succeeding other steps (for example, refining steps such as distillation, crystallization or the like). The heat generated in combustion of these waste gases and/or waste solution is recovered as the high pressure steam and/or the low pressure steam by using the steam generation apparatus. The utilization method of the high pressure steam and the low pressure steam may be the same as in the case of the above-mentioned reaction heat. The waste gas and/or the waste solution may be burned in one combustor, or the waste gas and the waste solution may be separately burned in each combustor. Further, combustors may be installed in the respective steps where the waste gas and/or the waste solution are generated. One or a plurality of the steam generation apparatuses for converting the heat generated in these combustors to steam may be used.

The high pressure steam, the low pressure steam A, and the low pressure steam B may be used as a power source and a heat source for various kinds of apparatuses which consume steam in the inside and outside of production plants in addition to the above-mentioned usages. It is preferable that the high pressure steam is supplied in priority to various kinds of apparatuses (for example, a blower, a compressor, and a pump) and driving appliances which require a relatively high temperature heat source, and that low pressure steams A and B are supplied to apparatuses such as a vacuum generator, a heat exchanger, a re-boiler, a heating apparatus, and the like, that are sufficient to be used relatively low temperature steam as a heat source. The supply of steam is not limited to the production plant of acrylic acid but also to places where steam is required such as an acrylic acid esterification plant and an acrylic acid polymerization plant.

EXAMPLE

Hereinafter, the present invention will be described in more detail by way of Examples. However it is not intended that the present invention is limited to the described examples. All the modifications and substitutions are included in the scope of the invention as long as not departing from the spirit and scope of the invention.

Examples

Acrylic acid was produced using propylene as a raw material. The reactor for a gas-phase catalytic oxidation reaction of propylene was a multi-tubular reactor divided in two stages of first and second. HTS (53 mass % of potassium nitrate+40 mass % of sodium nitrite+7 mass % of sodium nitrate: so-called "niter") was used as a heat medium for both of the first stage reactor and the second stage reactor. A reaction in the first stage reactor was carried out at 300° C. and a reaction in the second stage reactor was carried out at 260° C.

Most of the niter which had removed a reaction heat was supplied to a heat medium boiler, a steam generating apparatus, to generate high pressure steam at a pressure of 2 MPaG at 29.2 T/hr. After the high pressure steam at a pressure of 2 MPaG was further superheated using a part of the niter, the steam was supplied to a back pressure steam turbine for driving a blower which supplied molecular oxygen-containing gas to the reactor. The discharged steam of the turbine was superheated low pressure steam at a pressure of 0.6 MPaG (29.2 T/hr) and water was supplied to a part of the superheated low pressure steam to recover saturated steam (1) having a pressure of 0.6 MPaG at 0.3 T/hr.

Reaction product gas produced in the reactor was supplied to a waste heat boiler, a steam generating apparatus, to recover saturated steam (2) having a pressure of 0.6 MPaG at 0.8 T/hr. The reaction product gas discharged out of the waste heat boiler was supplied to an absorbing column to be caught in water. The concentration of acrylic acid in the collection solution obtained from the bottom of the column was 89.0 mass %. After being cooled in a condenser, a part of waste gas discharged from the top of the absorbing column was recycled to the reactor and the remaining was burned in a waste gas treatment equipment.

High pressure steam at a pressure of 4 MPaG was recovered at 11.7 T/hr from combustion heat generated by the waste gas burned. The high pressure steam at a pressure of 4 MPaG was consumed entirely in a neighboring water-absorbent polymer production facility. 12.1 T/hr of the steam from 30.3 T/hr of the steam in total of 29.2 T/hr of the low pressure steam at a pressure of 0.6 MPaG, which was the discharged steam of the back pressure steam turbine, 0.3 T/hr of the saturated steam (1) at a pressure of 0.6 MPaG, and 0.8 T/hr of the saturated steam (2) at a pressure of 0.6 MPaG, which was recovered by the waste heat boiler, was supplied to a regenerator of an absorption type refrigerator as a heat source, and then cold water was obtained. The cold water was used for crystallization step, which was a production (refining) step of acrylic acid. Furthermore, 6.6 T/hr of the steam was consumed in a re-boiler and a vacuum generator in the refining step of the acrylic acid production process. The remaining, that was 11.6 T/hr of the superheated low pressure steam, was supplied to a condensing turbine to obtain 1554 kW of electric power. The average electric power consumption of a pump or the like in the acrylic acid production process was about 1700 kW, and accordingly, electric power to be bought from the outside was able to be decreased to about 150 kW. No steam was purged to the atmospheric air without being consumed.

INDUSTRIAL APPLICABILITY

The production method of an organic acid of the invention comprises generating high pressure steam and low pressure steam method, and utilizing these steams directly for rotation energy of a blower and production of cold water by an absorption type refrigerator as a heat recovery. Therefore, heat utilization efficiency is improved as compared to in the case of once generating electric power from the steams and using the electric power for driving a blower or operating a refrigerator. Furthermore, since electric power is generated using excess low pressure steam, most of the electric power necessary in the process can be self-supplied.

The steam utilization method employed in the invention is applicable not only to the production process of acrylic acid but also to plants where an exothermal reaction is carried out at a high temperature.

What is claimed is:

1. A production method of an organic acid comprising the steps of;
   carrying out a gas-phase catalytic oxidation reaction of raw material gas with molecular oxygen at a temperature from 250° C. to 450° C.;
   collecting gas of an organic acid, a product of the gas-phase catalytic oxidation reaction with a liquid medium to produce an organic acid solution;
   cooling the organic acid solution by using cold water obtained in an absorption refrigerator to crystallize the organic acid;
   recovering at least a part of reaction heat generated in the gas-phase catalytic oxidation reaction and/or heat generated in combustion of a waste from the production of the organic acid as high pressure steam at a pressure of 1 MPaG or higher;
   supplying at least a part of the high pressure steam to a back pressure steam turbine connected with a blower which supplies the molecular oxygen to drive the blower; and
   supplying at least a part of discharged gas from the back pressure steam turbine, low pressure steam A at a pressure lower than 1 MPaG, to the absorption refrigerator to utilize the low pressure steam A as a heat source of the absorption refrigerator.

2. The production method of an organic acid according to claim 1, further comprising,
   supplying at least a part of the low pressure steam A to a condensing steam turbine of a power generator to obtain electric power.

3. The production method of an organic acid according to claim 1, wherein
   heat from a reactor for the gas-phase catalytic oxidation reaction is recovered by a heat medium, and
   the high pressure steam at a pressure of 1 MPaG or higher is produced by using the heat medium after recovering the heat from the reactor.

4. The production method of an organic acid according to claim 1, wherein,
   the gas of an organic acid, a product of the gas-phase catalytic oxidation reaction, is collected with a liquid medium to produce an organic acid solution containing 80 mass % or more of the organic acid.

5. The production method of an organic acid according to claim 1, wherein the organic acid is (meth)acrylic acid.

6. A production method of an organic acid comprising the steps of;
carrying out a gas-phase catalytic oxidation reaction of raw material gas with molecular oxygen at a temperature from 250° C. to 450° C.;
collecting gas of an organic acid, a product of the gas-phase catalytic oxidation reaction, with a liquid medium to produce an organic acid solution;
cooling the organic acid solution by using cold water obtained in an absorption refrigerator to crystallize the organic acid;
recovering at least a part of reaction heat generated in the gas-phase catalytic oxidation reaction and/or heat generated in combustion of a waste from the production of the organic acid as low pressure steam B at a pressure lower than 1 MpaG; and
supplying at least a part of the low pressure steam B to the absorption refrigerator to utilize the low pressure steam B as a heat source of the absorption refrigerator.

7. The production method of an organic acid according to claim 6, further comprising,
supplying at least a part of the low pressure steam B to a condensing steam turbine of a power generator to obtain electric power.

8. The production method of an organic acid according to claim 6, wherein,
the gas of an organic acid, a product of the gas-phase catalytic oxidation reaction, is collected with a liquid medium to produce an organic acid solution containing 80 mass % or more of the organic acid.

9. The production method of an organic acid according to claim 6, wherein the organic acid is (meth)acrylic acid.

10. A production method of an organic acid comprising the steps of;
carrying out a gas-phase catalytic oxidation reaction of raw material gas with molecular oxygen at a temperature from 250° C. to 450° C.;
collecting gas of an organic acid, a product of the gas-phase catalytic oxidation reaction, with a liquid medium to produce an organic acid solution;
cooling the organic acid solution by using cold water obtained in an absorption refrigerator to crystallize the organic acid;
recovering at least a part of reaction heat generated in the gas-phase catalytic oxidation reaction and/or heat generated in combustion of a waste from the production of the organic acid as high pressure steam at a pressure of 1 MPaG or higher;
supplying at least a part of the high pressure steam to a back pressure steam turbine connected with a blower which supplies the molecular oxygen to drive the blower;
recovering at least a part of the reaction heat and/or the heat generated in combustion of the waste as low pressure steam B at a pressure lower than 1 MPaG; and
supplying at least a part of the low pressure steam B and at least a part of discharged gas from the back pressure steam turbine, low pressure steam A at a pressure lower than 1 MPaG, to the absorption refrigerator to utilize the low pressure steam A and B as a heat source of the absorption refrigerator.

11. The production method of an organic acid according to claim 10, further comprising,
supplying at least a part of the low pressure steam A and/or the low pressure steam B to a condensing steam turbine of a power generator to obtain electric power.

12. The production method of an organic acid according to claim 10, wherein
heat from a reactor for the gas-phase catalytic oxidation reaction is recovered by a heat medium, and
the high pressure steam at a pressure of 1 MPaG or higher is produced by using the heat medium after recovering the heat from the reactor.

13. The production method of an organic acid according to claim 10, wherein,
the gas of an organic acid, a product of the gas-phase catalytic oxidation reaction, is collected with a liquid medium to produce an organic acid solution containing 80 mass % or more of the organic acid.

14. The production method of an organic acid according to claim 10, wherein the organic acid is (meth)acrylic acid.

15. The production method of an organic acid according to claim 4, wherein
the gas of an organic acid, a product of the gas-phase catalytic oxidation reaction, is collected with a liquid medium at an absorbing column, and
gas discharged from the absorbing column is recycled to the step of carrying out the gas-phase catalytic oxidation reaction.

16. The production method of an organic acid according to claim 15, wherein
the gas discharged from the absorbing column is cooled by a condenser and then recycled to the step of carrying out the gas-phase catalytic oxidation reaction.

17. The production method of an organic acid according to claim 8, wherein
the gas of an organic acid, a product of the gas-phase catalytic oxidation reaction, is collected with a liquid medium at an absorbing column, and
gas discharged from the absorbing column is recycled to the step of carrying out the gas-phase catalytic oxidation reaction.

18. The production method of an organic acid according to claim 17, wherein
the gas discharged from the absorbing column is cooled by a condenser and then recycled to the step of carrying out the gas-phase catalytic oxidation reaction.

19. The production method of an organic acid according to claim 13, wherein
the gas of an organic acid, a product of the gas-phase catalytic oxidation reaction, is collected with a liquid medium at an absorbing column, and
gas discharged from the absorbing column is recycled to the step of carrying out the gas-phase catalytic oxidation reaction.

20. The production method of an organic acid according to claim 19, wherein
the gas discharged from the absorbing column is cooled by a condenser and then recycled to the step of carrying out the gas-phase catalytic oxidation reaction.

* * * * *